United States Patent [19]
Bi

[11] Patent Number: 5,702,728
[45] Date of Patent: Dec. 30, 1997

[54] CLAM EXTRACT PREPARATION, THE METHOD OF PREPARATION AND USE THEREOF

[76] Inventor: Jieliang Bi, Room 301, Bldg. 31, Zhong Guancun Haidian District, Beijing 100080, China

[21] Appl. No.: 532,663

[22] PCT Filed: Apr. 15, 1994

[86] PCT No.: PCT/CN94/00026
 § 371 Date: Oct. 13, 1995
 § 102(e) Date: Oct. 13, 1995

[87] PCT Pub. No.: WO94/23731
 PCT Pub. Date: Oct. 27, 1994

[30] Foreign Application Priority Data

Apr. 17, 1993 [CN] China ............................. 93 1 03750.6

[51] Int. Cl.⁶ .................................................. A61K 35/56
[52] U.S. Cl. ........................... 424/547; 424/520; 424/522; 424/548

[58] Field of Search ............................... 424/520, 522, 424/547, 548

[56] References Cited

U.S. PATENT DOCUMENTS 4,550,020  10/1985  Rothman ............................. 424/184.1

OTHER PUBLICATIONS

Li et al., Cancer Chemotherapy Reports Part 2 vol. 4, No. 3 (Jul. 1974) pp. 97–129.
Li et al., Cancer Research 32: 1201–1205 (Jun. 1972).

*Primary Examiner*—Jean C. Witz
*Attorney, Agent, or Firm*—Sughrue, Mion, Zinn, Macpeak & Seas, PLLC

[57] ABSTRACT

The present invention relates to an extract of clam and the preparation method thereof. The clam extract can be used as analgesic agent and/or medicines for the inhibition the growth of tumors, especially for the treatment of cancers.

20 Claims, 1 Drawing Sheet

CLAM EXTRACT PREPARATION, THE METHOD OF PREPARATION AND USE THEREOF

TECHNICAL FIELD

The present invention relates to a clam (Lea) extract composition, its preparation method and medical applications, and a pharmaceutical composition containing the extract composition and the preparation method thereof.

BACKGROUND

For a long time, anodyne has been applied to relieve acute pains caused by cancer. The potent anodynes including, for example, dolantin and morphine are commonly used. Because of their side-effects such as leading to addiction etc., people have been trying to develop a new anodyne, which has strong and long-lasting pain-relieving effect but without side-effects such as leading to addiction.

The applicant, after long and careful researches, has developed a potent painkiller which can help patients, especially cancer patients of serious stages, relieve pains without the toxic side-effect, and no addiction has been observed. The applicant has further found that such analgesic can not only treat pains, but also inhibit the growth of tumors.

One objective of the present invention is to provide a clam extract composition, which has the effect of relieving pains on patients, particularly easing pains caused by cancer.

Another objective of the present invention is to provide a method of preparing the clam extract composition.

One further objective of the present invention is to provide a pharmaceutical composition containing the clam extract composition for treating pains.

Another objective of the present invention is to provide a clam extract composition with the effect of inhibiting the growth of tumor.

Other objectives of the present invention may be better understood from the description of the invention.

DISCLOSURE OF THE INVENTION

The clam extract composition of the invention made from clam (Lea) meat is in solid state under normal temperature and pressure and in light yellow, yellow or light brown color, which slightly dissolves in water or low density ethanol but hardly dissolves in organic solvents, such as ether, acetone, chloroform, benzene, acetic ester or n-butanol, etc., and has characteristic absorption between 250 nm to 278 nm shown by the ultraviolet absorption spectrum.

According to the present invention, a method of preparing a clam extract composition comprises the following steps:
grinding clam meat;
treating the grounded clam meat with acid and ethanol;
separating the mixture of acid, ethanol and claim meat to give a clear liquid;
concentrating the clear liquid to give the clam extract composition.

In the preparation, clam meat may be selected from various freshwater clams, and the preferred clam is Anodonta woodiana Lea, Cristaria plicata Lea, Hyriopsis cumingii Lea or a mixture thereof, including mixtures of two or three kinds of clams. Since the sources of clam are different, clam meat is washed with water before grinding to remove dirt or impurities, when necessary. Common grinding equipments, such as meat chopper or grinder, may be used to grind clam meat. In order to grind clam meat into a desired size, colloidal mill may also be used to re-grind the ground meat, or be directly applied to pulverize the clam meat. The smaller size of the ground clam meat is favorable to increase the output rate of extract from clam. Preferably, average size of the ground clam meat is less than 1 mm.

For the step of treatment with acid and alcohol, the used acid is $C_2$-$C_8$ fatty acid with straight chain or branched chain, preferably is $C_2$-$C_6$ fatty acid with straight chain or branched chain, such as acetic acid, citric acid or hydrochloric acid. The mixture of two or more than two kinds of acids may also be applied for the treatment. In the acid mixture, the proportion among the acids is optional. During the treatment with acid and alcohol, pH value shall be controlled at about 2 to 5.5. And the treatment with acid and alcohol is normally conducted under the normal temperature. The mixture is stirred during or after the addition of acid and alcohol, and the stirring may be ended when the mixture becomes homogeneous one. The treatment with acid and alcohol is normally carried out for 1 to 24 hours, preferably 5 to 12 hours. However, the next step can also be immediately begun after the sufficient acid is added.

In the treatment with acid and alcohol step, an adequate amount of ethanol is added. Alcohol may be added together with acid, or may also be added after acid is added. After the addition of ethanol, the density of alcohol shall be 40% to 75% of the acid treated materials.

The mixture treated with acid and alcohol is separated so as to obtain clear liquid. There are many separation methods, and the typical examples include centrifugal separation, filtering, suction filtering and filter pressing: The clear liquid obtained after separation can be concentrated in many ways, such as ultra-filtering, reserve osmosis and vacuum concentration, ect.

In accordance with the present invention, clear liquid obtained after separation may be treated with alkali instead of the concentration step, for instance, using NaOH or KOH in the treatment. pH value of the mixture is maintained at 8 to 13 during the alkali treatment. The alkali treatment period is normally controlled within 24 hours. An additional amount of ethanol may also be added. Ethanol may be added together with alkali or after alkali is added. For the alkali treatment, the density of ethanol can be maintained at 75% to 90%. The precipitate separated after alkali treatment is clam extract composition. The separation methods are the same as those described above.

According to the present invention, the clam extract composition obtained after the concentration step, or clam extract composition obtained after the alkali treatment step may undergo the step of dehydration and drying. The common dehydration and drying methods include: dehydration by reagent such as ether and acetone, etc., freeze drying dehydration and spray drying, ect. Additional acid may be added to the extract of clam obtained with the alkali treatment before the dehydrating and drying step to adjust the pH value of the clam extract composition, except for the dehydrating by reagent. The pH value normally ranges from 4 to 7, and the acid to be used is the same as that mentioned above.

Clam extract composition prepared according to the method of the invention may be further purified by re-undergoing the above-mentioned acid treatment and the steps which follow the acid treatment. The process may be repeated many times, and the acid used may be same or different.

Another preparation method of clam extract composition according to the present invention includes the following steps:

grinding clam meat;

treating the ground clam meat with heat in the present of acid and water;

separating the heat-treated mixture to obtain clear liquid;

concentrating the clear liquid to obtain clam extract composition.

The size of ground clam and the grinding methods used are same as those mentioned above. During the heat treatment step, an adequate amount of water is added. The added acid shall make pH value of the material to be treated ranging from 2.0 to 6.0. The acid to be used is the same as that mentioned above. The temperature of heat treatment is normally maintained at 48° to 88° C. and the heating period is 0.5 to 4.5 hours.

Clam extract composition obtained from the concentration may be further dehydrated and dried. The methods for separation, concentration and dehydration and drying are the same as those described above. The steps of the heat treatment method for the preparation of clam extract composition may be repeated in order to purify the clam extract composition.

Method to identify clam extract composition prepared according to the invention.

1 g sample of clam extract composition prepared according to the invention was taken. Water was added to 50 ml. The mixture was filtered and then the filtrate was obtained for the following identification (1,2,3 and 4).

1. 2 ml of the filtrate was added into a test tube. 3 to 4 drops of 5% of α-naphthol alcohol was added, and the mixture was shaken to be homogeneous, and then 1 ml of concentrated sulfuric acid was added slowly along the wall of the test tube. Purple rings appeared on the connection of the two liquid phases.

2. The filtrate in an appropriate amount was taken and the same volume of 3,5-dihydroxytoluene solution was added. The mixture was shaken to be homogeneous and heated in water bath for 10 minutes. Then green color appeared.

3. 2 ml of the filtrate was added into a test tube, and drops of iron trichloride-potassium ferricyanide solution was added, and blue color appeared immediately.

4. 2 ml of the filtrate was added into a test tube, and barium hydroxide solution was added. Flock in light yellowish color appeared.

5. 1 g sample of the clam extract composition prepared according to the invention was put into a conical flask. 15 ml of 10% sulfuric acid solution was added. A small glass funnel was inserted into the mouth of the flask, and the mixture was heated for hydrolysis in boiling water bath for about half an hour. Then the mixture was filtered and the filtrate was taken for the following tests:

(1) 1ml of 0.1 N $AgNO_3$ solution was added into a test tube, then 1N ammonia water was added gradually in drops until the precipitate disappeared. And then 1 ml of the above filtrate was added. The mixture was left to stand for a while, and white precipitate appeared in the sample prepared according to the invention, which becomes red-brown under light.

(2) 2 ml of the filtrate was added into a test tube. After 5 drops of strong nitric acid and 1 ml of ammonium molybdate was added, yellow precipitate appeared in the sample when heated in the boiling water bath.

(3) 1 ml of the filtrate was added into a test tube, and the same volume of 3,5-dihydoxy toluene solution was added. The sample became green when heated in the boiling water bath for 10 minutes.

Figure 1D:
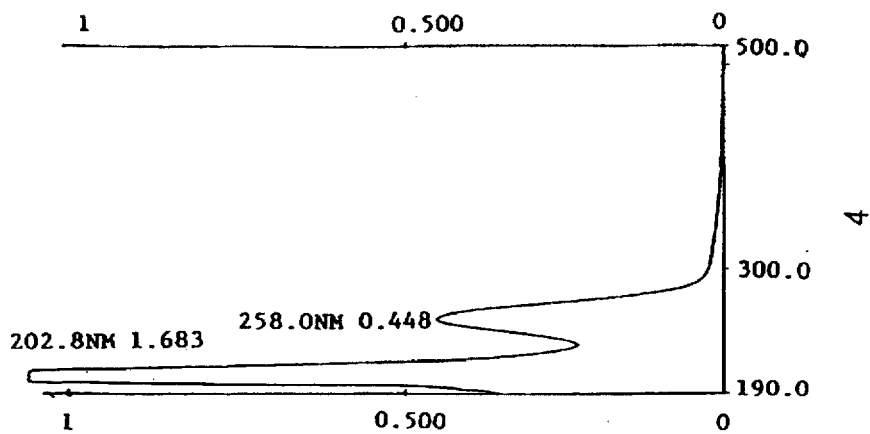
FIG. 1 is the ultraviolet-visible light absorption spectrum of clam extract composition prepared according to the invention.
Figure 1C:
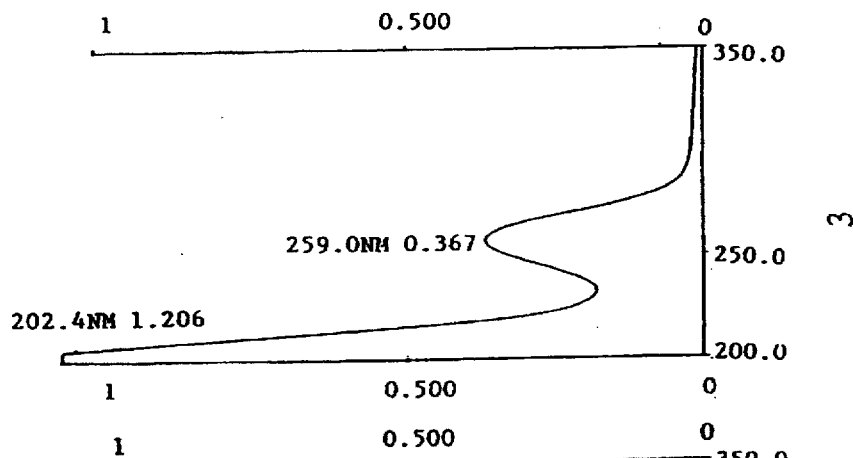
Figure 1B:
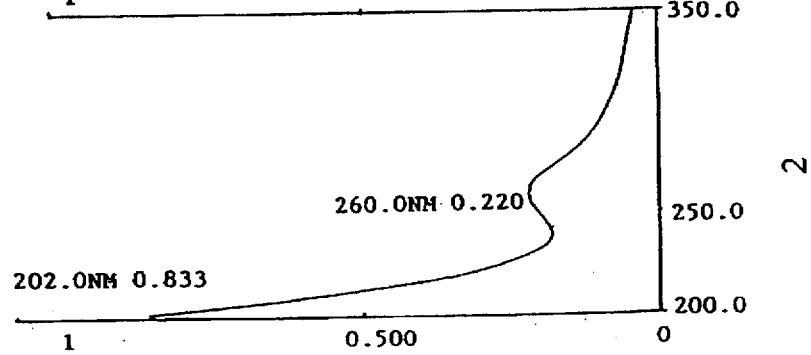
Figure 1A:
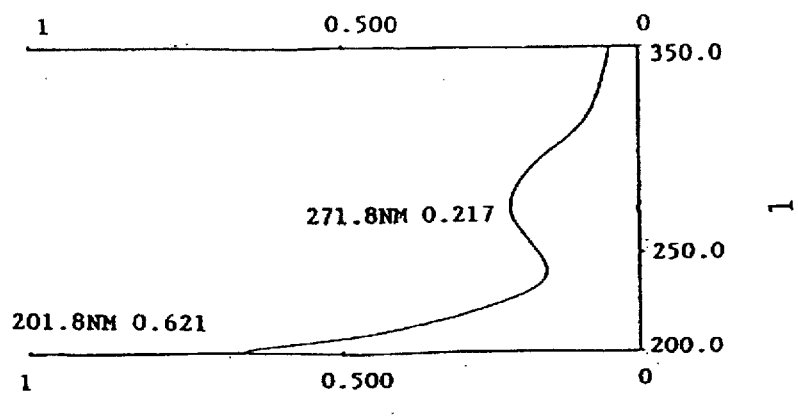

6. Ultraviolet-visible light absorption characteristics:

The sample extract composition prepared according to the invention in an appropriate amount was taken and dissolved in normal saline, and analysis was carried out according to the spectrophotometry (page 24 of the appendix to the second portion of Chinese Pharmacopoeia 1990 edition). The ultraviolet absorption spectrum is shown as in FIG. 1.

It can be seen from the test results that the four batches of clam extract composition show the maximum absorption at 258 nm, 259 nm, 160 nm and 271 nm respectively. In view of the difference in size, sources and species of clams, their characteristic absorptions are in the range from 250 nm to 278 nm of ultraviolet absorption spectrum.

The present invention also includes clam extract composition prepared according to any one of the methods of the invention.

Clam extract composition of the invention can be used as analgesic to ease various pains in the medical field, such as pains after surgery, pains caused by rheumatic diseases, toothache, pains caused by injuries and burns, especially pains caused by serious stages of cancer, etc. The clam extract composition of the invention has a longer pain-relieving effect than anodynes which are commonly used at present. At the same time, the clam extract composition of the invention can also ease the clinic symptoms of cancer patients in serious stage, prolong the life of the patients, and improve the joint positions of rheumatic patients. During clinic applications, no addiction to the clam extract composition has been found.

The clam extract composition of the invention also has the effect on inhibiting the growth of tumor, and can be used to treat and cure various tumors, including cancer at the most serious stage, or can also be used together with other drugs to treat and cure cancer, particularly malignant tumors, as a supplementary drug.

The clam extract composition of the invention can also be used as analgesic and tumor-inhibitor at the same time. The extract composition while treating pains of patients, can also inhibit the growth of tumors.

Acute Toxicity Test

I. Testing Materials

1. Animals: Wistar rat, each weighting 240–250 g with male and female each in half, provided by Animals Laboratory of Chinese Academy of Medical Sciences.

2. Specimen: the suppository prepared by the clam extract composition of the present invention (0.15 g/pc).

II. Testing Methods and Results 20 healthy Wistar rats were randomly divided into two groups (i.e, test group and control group) based on the body weight, with 10 rats in each group and male and female each in half. Each Wistar rat in the test group was intrarectally administered 1.2 g/kg of the specimen which contacted the mucous membrane for more than 4 hours. For the control group, one piece of excipient was administered according to the above rectal medication. Then the rats were observed for changes on their whole bodies, such as diet, activity of arms and legs, excretion, body weight, etc., for 7 successive days. The results are as the followings:

TABLE 1

Results of Acute Toxicity Test of the Clam Extract Composition

| | | | | | State of rats after administration | | | | |
|---|---|---|---|---|---|---|---|---|---|
| Group | Number of animals | Administration route | Dosage (g/kg) | Time (day) | Body weight | Diet | Activity of arms & legs | Excretion | Death |
| Test | 10 | by Rectum | 1.2 | 7 | ↑ | — | — | — | 0 |
| Control | 10 | by Rectum | 1 pc | 7 | ↑ | — | — | — | 0 |

Note:
"↑" stands for increase,
"—" stands for normal.

III. Conclusion:

No toxic reaction has been observed after the rats had intrarectally been administered with the specimen in the dosage of 1.2 g/kg.

Irritating Test of Rectum

I. Testing Materials

1. Animals: Wistar rats, each weighting 240–280 g with male and female each in half, provided by Animals Laboratory of Chinese Academy of Medical Sciences.

2. Specimen: the suppository prepared by the clam extract composition of the present invention (0.15 g/pc).

II. Testing Methods and Results 20 healthy Wistar rats were randomly divided into two groups (i.e. test group and control group) based on the body weight, with 10 rats in each group and male and female each in half. Each Wistar rat in the test group was intrarectally administered 1.2 g/kg of the specimen which contacted the mucous membrane for more than 4 hours. For the control group, water in equal quantity was administered according to the above rectal medication once a day for 7 successive days. Then the rats were killed after 24 hours from the last administration. The rectum tissue was taken and observed macroscopically whether symptoms such as congestion, rubifaction and tumefaction etc. appear in the mucous membrane. The results are shown in Table 2.

Study on Analgesic Effects

I. Purpose of the Test

The purpose of the test is to observe effects of the suppository prepared by the clam extract composition of the invention on pains of mice caused by chemical and electric irritation, and the time of initiation and duration of the effect.

II. Testing Materials and Animals

1. Drugs:

The clam extract composition of the invention was dissolved in 2 mol acetic acid and the pH value was adjusted to be 6.5–7.0. Then normal saline in an adequate amount was added.

Indomethacin: produced by Nantong Second Pharmaceutical Factory, with the lot number of 860321, which was formulated into a suspension with 2% of water-soluble starch paste.

3. Instruments:

An electric stimulator of Model NEN-7103, and an isolator of Model SS-102J, made in Japan.

III. Testing Methods and Results

1. Effects on the Body Torsion Reaction of Mice Caused by Acetic Acid

After fasting for 12 hours, 60 mice were randomly allotted into 6 groups based on their body weight and sex. The drug was intrarectally administered in the dosage indicated in

TABLE 2

Results of Irritating Test of Rectum

| | | | | | State of rectal mucosa after dissection | |
|---|---|---|---|---|---|---|
| Group | Number of animals | Administration route | Dosage (pc) | Time (day) | congestion | rubifaction & tumefaction |
| Test | 10 | by Rectum | 1 | 7 | — | — |
| Control | 10 | by Rectum | 1 | 7 | — | — |

Note:
"—" stands for negative reaction

III. Conclusion:

It can be seen from Table 2 that no irritated symptoms such as congestion, rubifaction and tumefaction has been observed in the mucous membrane after the rats are intrarectally administered with 1 piece of suppository of the invention per rat for 7 successive days.

Table 3 and the volume of drug administered was 0.05 ml per mouse. 35 minutes later, 0.20 ml of 0.6% acetic acid was intraperitoneally injected to each mouse. The number of body torsion reactions (abdominal excavation, extension of trunk and hind limbs, and elevation of buttock) observed within 15 minutes after the injection of acetic acid was recorded.

TABLE 3

Effects of Intrarectally Administered Suppository of the
Invention on Body Torsion Reaction of Mice Caused by Acetic Acid

| Group | Dosage (mg/kg) | Number of animals | Number of body torsions (n) | Inhibition rate (%) |
|---|---|---|---|---|
| Control | N.S. | 12 | 39.3 ± 14.4 | |
| Indomethacin | 7.5 | 12 | 2.7 ± 4.1 | 93.1 |
| Suppository of the invention | 140.0 | 12 | 17.8 ± 12.2* | 54.7 |
| Suppository of the invention | 198.0 | 12 | 15.1 ± 7.2* | 61.6 |
| Suppository of the invention | 280.0 | 12 | 2.3 ± 3.6* | 94.1 |

*Compared with the control group, $P < 0.01$

The results show that the suppository of the invention can remarkably reduce the number of body torsions of mice caused by acetic acid. The inhibition rate was 54.7% when the dosage of intrarectal administration was 140.0 mg/kg (which was converted by 1.0 g/60 kg for human when administered intrarectally once, according to the method of dosage conversion by Xu Shuyun et al. in "Methodology of Pharmacological Experiments, 2nd edition, pp. 178~180, published by People's Health Press, Nov. 1991, Beijing), and the inhibition rate was positively correlated with the dosage. The results indicate that the suppository of the invention can inhibit pains of mice caused by chemical irritation and has analgesic effects.

2. Effects on Pains Caused by Electric Irritation to Tails of Mouse

After fasting for 12 hours, 50 mice were randomly allotted into 5 groups based on their body weight and sex. The root of mouse's tail was stimulated with electric current of square wave (10 ms of pulse width and 1 Hz of the frequency). The pain threshold was determined as the electric intensity which just makes the mouse screaming. The drug was intrarectally administered with the volume of 0.05 ml per mouse. The dosage administered is listed in Table 2. The effect on pains was determined respectively at 20, 40, 60 and 120 minutes after the medication, and the analgesic percentage of the test group was calculated as followings:

$$\frac{\text{Threshold after medication} - \text{Threshold before medication}}{\text{Threshold before medication}} \times 100$$

The results show that the suppository of the invention can increase the pain threshold of mice in a dosage-dependence manner when administered intrarectally (see Table 4). The initiation time of analgesic effects was negatively correlated with dosage of the drug, while the duration of the effect was positively correlated with the dosage. The time of analgesic effects in maximum appeared at 60 minutes after the medication (see Table 5). No drug addiction was observed.

TABLE 4

Effects of Suppository of the Invention Administered Orally on the Pain Threshold of Tail Roots of Mice Caused by Electric Irritation

| Group | Dosage (mg/kg) | Number of animals | Before medication | Pain threshold (mA X ± SD) on different time (min) | | | | |
|---|---|---|---|---|---|---|---|---|
| | | | | 20 | 40 | 60 | 90 | 120 |
| Control | N.S. | 10 | 0.24 ± 0.08 | 0.25 ± 0.08 | 0.28 ± 0.11 | 0.26 ± 0.13 | 0.26 ± 0.13 | 0.25 ± 0.11 |
| Indomethacin | 7.5 | 10 | 0.22 ± 0.08 | 0.32 ± 0.06* | 0.41 ± 0.12* | 0.44 ± 0.15* | 0.41 ± 0.13* | 0.38 ± 0.13* |
| Suppository of the invention | 140.0 | 10 | 0.22 ± 0.02 | 0.26 ± 0.04 | 0.33 ± 0.06 | 0.34 ± 0.08 | 0.30 ± 0.07 | 0.29 ± 0.08 |
| Suppository of the invention | 198.0 | 10 | 0.25 ± 0.07 | 0.32 ± 0.10 | 0.34 ± 0.12 | 0.36 ± 0.10 | 0.38 ± 0.09* | 0.33 ± 0.09 |
| Suppository of the invention | 280.0 | 10 | 0.23 ± 0.09 | 0.32 ± 0.11 | 0.41 ± 0.11* | 0.44 ± 0.10** | 0.41 ± 0.13* | 0.45 ± 0.22* | t-Test, compared with the control group: *$P < 0.05$, **$P < 0.01$

TABLE 5

Increasing Percentage of the Pain Threshold of Tail Roots of Mice Caused by
Electric Irritation after Administered Intrarectally with the Suppository of the Invention

| Group | Dosage (mg/kg) | Number of animals | Increasing percentage of the pain threshold on the different time (min) | | | | |
|---|---|---|---|---|---|---|---|
| | | | 20 | 40 | 60 | 90 | 120 |
| Control | N.S. | 10 | −0.24 ± 18.1 | 7.76 ± 27.5 | 7.19 ± 35.8 | −4.14 ± 37.4 | 0.024 ± 32.5 |
| Indomethacin | 7.5 | 10 | 37.4 ± 18.4* | 71.4 ± 39.4* | 86.3 ± 45.9* | 72.5 ± 59.1* | 69.6 ± 62.3* |
| Suppository of the invention | 140.0 | 10 | 21.5 ± 18.4* | 32.0 ± 12.5* | 43.1 ± 25.6* | 40.5 ± 36.5* | 34.5 ± 31.8* |
| Suppository of the invention | 198.0 | 10 | 32.4 ± 10.8* | 34.3 ± 8.7* | 52.8 ± 16.2* | 66.6 ± 33.1* | 39.4 ± 31.9* |
| Suppository of the invention | 280.0 | 10 | 42.5 ± 31.4* | 90.9 ± 43.1* | 107.7 ± 53.0* | 99.2 ± 71.3* | 101.7 ± 81.7* | t-Test, compared with the control group: *$P < 0.01$

Analgesic Effects of Clam Extract Composition of the Invention Administered Orally on Pains in Mice Caused by Chemical Irritation.

I. Testing Materials

1. Drugs:

Clam extract composition of the invention was dissolved in 2N acetic acid and the pH value was adjusted to be 6.5~7.0. The normal saline in an adequate amount was added to formulate a solution. Indomethacin: produced by Shijiazhuang Pharmaceutical Factory, with the lot number of 009011021, which was formulated into a suspension with 2% of starch paste.

2. Animals:

Kunming strain mice, male and female, with body weight of 20±2 g, provided by the Department of Animals of Beijing Medical University.

II. Testing Methods and Results

Fifty mice were randomly allotted into 5 groups based on their body weight and sex. In the control group, 0.2 ml/kg body weight of normal saline was administered per oral; while in the positive group, 30 mg/kg of indomethacin was administered per oral. In other three groups, 1 g/kg, 2 g/kg and 4 g/kg of the solution of the invention were administered per oral respectively. 90 minutes later, 0.2 ml of 0.6% acetic acid per mouse was intraperitoneally injected and the number of body torsion reactions (abdominal excavation, extension of trunk and hind limbs, and elevation of buttock) of the mouse observed within 15 minutes after the injection of acetic acid was recorded.

TABLE 6

Effects of Solutions of the Invention Administered Orally on Body Torsion Reaction of Mice Caused by Acetic Acid

| Group | Dosage (mg/kg) | Number of animals | Number of body torsions (n) | Inhibition rate (%) |
|---|---|---|---|---|
| Control | N.S. | 10 | 44.1 ± 12.8 | |
| Indomethacin | 0.03 | 10 | 2.8 ± 4.8* | 93.7 |
| Solution of the invention | 1.0 | 10 | 24.8 ± 12.2* | 43.8 |
| Solution of the invention | 2.0 | 10 | 17.5 ± 7.1* | 60.3 |
| Solution of the invention | 4.0 | 10 | 4.3 ± 4.6* | 89.2 |

*Compared with the control group, *P < 0.01

The results of Table 6 show that the solution of the invention can remarkably reduce the number of body torsions of mice caused by acetic acid and the inhibition effect is positively correlated with the dosage, which indicate that the clam extract composition of the invention can inhibit pains of mice caused by chemical irritation and has analgesic effects.

Inhibition Rate of Clam Extract Composition on Tumor of Ehrlich's Ascites Carcinoma in Mice Testing Animals: Female Kunming strain mice with 18~21 g of body weight. Tumor Model: Ehrlich's Ascites Carcinoma (EAC) Drugs: Clam extract composition prepared according to the method of the invention from Cristaria plicata Lea, which was dissolved in normal saline. The solution of clam extract composition was adjusted to be pH6.5, and was then sterilized and filtered.

Testing Methods:

A. Inoculation: Take the white ascites which was previously produced in mice by inoculating Ehrlich's Ascites Carcinoma and cultivating for one week, to which normal saline was added in a proportion as 1:2 (white ascites: normal saline). Then 0.2 ml of the mixture was subcutaneously injected at axillary fossa.

B. Grouping: On the next day after the inoculation, mice were randomly allotted into 4 groups wherein the three groups (group 2,3 and 4) were administered daily with 1 g/kg, 1.5 g/kg and 2 g/kg respectively. While the negative control group (group 1) were administered with normal saline in a corresponding equivalent amount.

C. Administration Route: Oral administration, once per day for successive 6 days.

D. Evaluation of Affects: 24 hours after stopping medication, mice were killed and their body weight were weighed. The tumor mass was also weighed after being stripped.

$$\text{Inhibition Rate of Tumor} = \frac{C-T}{T} \times 100$$

Wherein T means the average weight of tumor in the medication group and C means the average weight of tumor in the control group.

Inhibition Rate of Solution of the Invention Administered Orally to Mice on Ascites Tumor of Ehrlieh's Carcinoma.

| | Number of mice | | | Body weight | | Average weight of tumor | Inhibition rate of tumor (%) | P value |
|---|---|---|---|---|---|---|---|---|
| Number of group | At the beginning | At the end | Mortality (%) | At the beginning (g) | At the end (g) | | | |
| 1 | 15 | 15 | 0 | 19.2 | 21.6 | 1.12 | 0 | |
| 2 | 15 | 15 | 0 | 19.0 | 21.1 | 0.77 | 31.6 | 0.05 |
| 3 | 15 | 15 | 0 | 19.5 | 21.9 | 0.53 | 52.5 | 0.01 |
| 4 | 15 | 15 | 0 | 19.1 | 22.0 | 0.58 | 48.4 | 0.01 |

The results (see Table 7) show that the inhibition rate of the extract composition according to the invention for Ehrlich's ascites carcinoma (EAC) can achieve 31.6%~52.5%.

The pharmaceutical composition according to the invention comprises an effective amount of clam extract composition of the invention and a pharmaceutically acceptable carrier and/or assistant agent. The carriers and/or assistant agents used are conventional ones.

The administration routes of the pharmaceutical composition of the invention may be per oral, injection, local application or intracavitary medication. For oral administration, a dose of 0.5~2 g for each time and 2 to 4 times a day is used for an adult. For injection, a dose of 100~300 mg for each time and 2 to 4 times per day is used for an adult. When the drug is administered intracavitarily, a dosage of 0.1~0.5 g each time and 2~4 times a day is used for an adult. An adequate amount of drug is used for local application.

Various preparation forms can be made from the pharmaceutical composition of the invention, such as tablets, sugar-coated enteric soluble tablets, capsules, e.g. gastric soluble capsules and enteric soluble capsules, suppositories, oral liquid, microcapsules, ointments, water solutions, powder injections or injections, etc.

According to the invention, a method of analgesia and treatment of tumor or carcinoma, comprises administrating to patients an effective amount of the clam extract composition of the invention.

The clam extract composition of this invention may also be formulated into tablets, capsules, decoctions, oral solutions and other preparation forms in combination with other drugs or extracts, such as Radix Arnebiae seu Lithospermi, Radix Notoginseng, hydrolyzed pearl powder, solution of Cordyceps sinensis, Indigo Naturalis, Radix Polygalae, Semen Ziziphi Spinosae extract of Lentinus edodes (berk) sing, glycerin extract, etc. not only to achieve the above-mentioned objections, but also to broaden applications, such as treatment of scald, prevention of infection, treatment of diseases of cardiovascular system, abdominal pain, insomnia, etc., and to strengthen immunity, constitution and function of human body, etc.

Clinical Test 1

I. Test Drug:

Suppository (1 g/dose) prepared from clam extract composition of the invention.

II. Dosage:

One dose at each time and two times a day for successive 3 days. The suppository was inserted into rectum above anus 5 cm.

III. Selection of Patients:

Cancer patients with moderate or severe pain.

IV. Method of Pain Grading:

Grading was made according to VAS and VRS methods.

Grading of pain relief: remarkably effective, effective, and non-effective were graded.

V. General Information:

Up to February, 1994, a total of 10 cases were observed and used. Among them 7 were male and 3 were female. Their ages ranged from 25 to 76. Diagnosis: pulmonary carcinoma: 6 cases; esophageal carcinoma, adenocarcinoma of pancreas, malignant lymphoma, and pituitary tumor: one case each.

VI. Observation on Analgesic Effect:

| Grade of Pain | Number of cases | Remarkably effective | Effective | Non-effective | Effective rate |
|---|---|---|---|---|---|
| Mild | | | | | |
| Moderate | 2 | 2 | | | |
| Severe | 8 | 1 | 6 | 1 | |
| Total | 10 | 3 | 6 | 1 | 90% |

In most of above cases, analgesic effect began to appear within 1~2 hours after medication and the duration of pain relief varied from 8 to 24 hours.

VII. Typical Case Report:

Patient A: male, 59 years old, suffered from pulmonary carcinoma of the right lung with metastasis to retroperitoneal lymph nodes and right adrenal gland. The adenocarcinoma was diagnosed by pathology. His chief complaint was pains at upper abdomen and waist with disturbed sleep. He had been treated with Dihydroeprophy (DHP). At first 4~6 tablets per day were administered, then the treatment was changed by using suppository of the invention, one dose a time intrarectally, 2 times per day. Pain disappeared completely during treatment and the clinical evaluation was a complete pain relief. Administration was stopped after treatment for 3 successive days. The patient asked for continuation of intrarectal administration for analgesia.

VIII. No toxic side effect of the suppository of the invention has been observed in the above-mentioned clinical application. It was effective in treating pain caused by tumor, and the effective rate was 90%.

Clinical Test 2

From November, 1993 to January, 1994, the suppositories made from clam extract composition of the invention were used to treat 20 patients (43 cases) with pain complicated or/and accompanying with various cancers. The information of observation is as follows:

I. General Clinical Data:

1. Sex and age: In this 20 patients, 13 were male and 7 were female. The minimal age was 30 and maximal 76 (median age 54.2).

2. Selection of patients (1) Patients suffered from various kinds of cancers which had all been confirmed by histopathology or/and cytology, and the complications such as bone metastasis had all been confirmed by roentgenogram, ECT or CT examination.

(2) Radiotherapy had not been applied or chemotherapy regime had not been changed during recent 4 weeks.

The pathologic types and pain complicated or/and accompanying cancer in these 20 patients were as follows:

A. Pulmonary carcinoma, 8 cases (adenocarcinoma, 5 cases; small cell carcinoma, 3 cases). The pain was induced by bone metastasis in 5 cases, accompanying chest pain in 2 cases, and concomitant urinary lithiasis in 1 cases. Malignant mesothelioma on right pleura was diagnosed in one patient.

B. Tumor of digestive tract, 4 cases (gastric carcinoma, 3 cases; colon cancer, 1 case).

The pain was all induced by hepatic metastasis. In two patients with primary carcinoma of liver, one had pain at hepatic region and the pain in the other patients was caused by bone metastasis of cancer.

C. Mammary cancer, 4 cases. Accompanying pain caused by periarthritis of shoulder in one case and by occult cleft of spine of sacral vertebrae in another one. In the other two patients pain was induced respectively by metastasis of cancer to chest wall and to left hip bone.

D. Prostatic carcinoma, 1 case. The pain was induced by multiple bone metastasis after surgical operation.

II. Methods of Treatment and Observation

1. Suppository of the invention (1) Administration: One dose (containing 1 g of drug/dose) at a time was inserted into the rectum, 5 cm above anus.

(2) Dosage: One dose (1 g) a time, two doses per day. One course of treatment lasted 1 to 3 days. Pain was evaluated separately at 0.5, 1, 2, 3, 4, 5, 6, and 7 hours after administration.

2. Symptoms were recorded and biochemical monitoring was performed in all patients. The symptoms included pain, mobility, nausea and vomiting, appetite and defecation, etc. Blood biochemical tests included routine examinations of blood, platelet count, concentrations of potassium, sodium, chlorine, calcium, phosphorus, transaminase, urea nitrogen creatinie, globulin, alkaline phosphatase, transpeptidase, and etc. in blood.

III. Results of Treatment and Observation:

1. Grading criteria for clinical index, based on the streaking method (VAS) and on grading by subjective complaint of pain (VRS): 0 means painlessness; 1~3 means mild pain that can be tolerated by patients, whose daily life and sleep are normal; 4~7 means moderate pain which disturbs sleep of patients and patients ask for analgesics; 8 or up means severe pain which greatly disturbs sleep of patient and should be treated with narcotics. In this test, 5 patients had mild pain, 10 had moderate pain, and 5 had severe pain.

2. Criteria for evaluation of the therapeutic effects:

Complete relief: Patients do not suffer from pains at all. Remarkable relief: The severity of pain is evidently lessened compared with that before medication, and the patients can live normally without sleep disturbing essentially. Slight relief: The severity of pain is lessened somewhat than that before medication, however, there is still remarkable pain, and sleep is still disturbed. No effect: There is no difference in severity of pain before and after medication.

3. Therapeutic effects:

(1) Analgesia: In the above 20 patients, complete relief was observed in 5 cases, remarkable relief in 12 and slight relief in 2. The overall effective rate was 95.0%.

(2) Time of initiation of analgesic effect: Analgesic effect appeared at half an hour after administration in all of these 20 patients.

(3) Time of the best analgesic effect: It appeared mostly at 2~5 hours after administration.

(4) Duration of analgesic effect: The longest duration was 10 hours, which was longer than that of indomethacin suppository.

(5) Analgesia and the time of administration: The analgesic effect was better when the drug was administered more frequently than less frequently.

(6) The observation result of analgesic effect is shown in the following table:

| Grade of pain | Number of patient | Remarkable effective | Effective | Non-effective | Effective rate |
|---|---|---|---|---|---|
| Mild | 5 | 4 | | 1 | 80% |
| Moderate | 10 | 9 | 1 | | 100% |
| Severe | 5 | 4 | 1 | | 100% |
| Total | 20 | 17 | 2 | 1 | 95% |

4. Side-effect:

No noxious side-effect on kidney and liver functions was observed. The number of defecation times increased or urgency of defecation occurred in some individual patients after medication. In the 20 patients treated, one defecated immediately, 7 defecated an hour after medication, and the rest 12 patients could defecate 2 or more than 2 hours after medication by self-control. No anus irritation and other phenomena were observed.

One patient experienced weakness of lower limbs, who was a 76 years old Suffering from bone metastasis of prostatic carcinoma. His severe pain relieved evidently after medication. However, weakness of lower limbs appeared after 3 times of medication and inability to stand up due to weakness of the legs after 5 times of medication. But, weakness of legs disappeared quickly after stopping medication.

The preparation method of the clam extract composition according to the invention will be further described in detail in the following examples, but the scope of the invention does not limit to these examples.

EXAMPLE 1

Clam meat from 3 kg of Cristaria plicata Lea was taken and smashed with TM-85 Model colloidal mill to particles of average diameter of 10μ. pH value was adjusted to 3.85 with acetic acid under stirring, then 2000 ml of ethanol was added, and kept still for 8 hours after stirred homogeneously. The supernatant was taken and the pH value of the supernatant was adjusted to 13 with NaOH. Ethanol was added till its content reached 75%. Then the mixture was stirred homogeneously and kept stand for 8 hours. The precipitate was taken and acetic acid was added till the pH value was 6.0. A faint yellow extract composition was obtained after freeze drying. The productive rate was 0.18% of the original clam weight.

EXAMPLE 2

2 kg of clam meat from Anodonta woodiana Lea was taken. A faint yellow extract composition was obtained by the preparation method same as Example 1. The productive rate was 16% of the original clam weight.

EXAMPLE 3

Clam meat from 6 kg of Hyriopsis cumingii Lea was taken. A faint yellow extract composition was obtained by the preparation method same as Example 1. The productive rate was 0.08% of the original clam weight.

EXAMPLE 4

Clam meat from total weight 6 kg of Cristaria plicata Lea and Anodonta woodiana Lea was taken. A faint yellow extract composition was obtained by the preparation method same as Example 1. The productive rate was 0.17% of the original clam weight.

EXAMPLE 5

Clam meat from 4 kg of Hyriopsis cumingii Lea was taken. A light brown extract composition was obtained by the preparation method similar to Example 1 except that the period of standstill was 24 hours. The productive rate was 0.08% of the original clam weight.

EXAMPLE 6

Clam meats from 7 kg of Cristaria plicata Lea were taken. A faint yellow extract composition was obtained by the preparation method similar to Example 1 except that the standstill was replaced by taking supernatant directly. The productive rate was 0.18% of the original clam weight.

EXAMPLE 7

Clam meats from total weight 9 kg of Cristaria plicata Lea, Anodonta woodiana Lea, Hyriopsis cumingii Lea were taken. A faint yellow extract was obtained by the preparation method same as Example 1. The productive rate was 0.21% of the original clam weight.

EXAMPLE 8

Clam meats from Cristaria plicata Lea, Anodonta woodiana Lea, Hyriopsis cumingii Lea, each weighting 3 kg, were taken. A faint yellow extract composition was obtained by the preparation method similar to Example 1 except that 2 mol of hydrochloric acid was used instead of acetic acid. The productive rate was 0.37% of the original clam weight.

EXAMPLE 9

Clam meats from Cristaria plicata Lea and Anodonta woodiana Lea, each weighting 3 kg, were taken. A faint yellow extract composition was obtained by the preparation method similar to Example 1 except the pH was adjusted by citric acid. The productive rate was 0.42% of the original clam weight.

EXAMPLE 10

Clam meat from 3 kg of Cristaria plicata Lea was taken. A faint yellow extract composition was obtained by the preparation method similar to Example 1 except the pH was adjusted to 2.15 with acid. The productive rate was 0.20% of the original clam weight.

EXAMPLE 11

Clam meat from 3 kg of Anodonta woodiana Lea was taken. A faint yellow extract composition was obtained by the preparation method similar to Example 1 except that the ethanol added was 1800 ml. The productive rate was 0.36% of original clam weight.

EXAMPLE 12

Clam meat from 3 kg of Cristaria plicata Lea was taken. A faint yellow extract composition was obtained by the preparation method similar to Example 1 except that the added ethanol was 1500 ml. The productive rate was 0.24% of the original clam weight.

EXAMPLE 13

Clam meat from 3 kg of Cristaria plicata Lea was taken. A faint yellow extract composition was obtained by the preparation method similar to Example 1 except that no ethanol was added after the alkali was added. The productive rate was 0.14% of the original clam weight.

EXAMPLE 14

Clam meat from 3 kg of Cristaria plicata Lea was taken. A faint yellow extract composition was obtained by the preparation method similar to Example 1 except that 2N of KOH was added instead of NaOH. The productive rate was 0.14% of the original clam weight.

EXAMPLE 15

Clam meat from 3 kg of Critaria plicata Lea was taken. A faint yellow extract composition was obtained by the preparation method similar to Example 1 except that no alkali and no ethanol in alkali treatment step was used. The productive rate was 0.22% of the original clam weight.

EXAMPLE 16

Clam meat from 3 kg of Cristaria plicata Lea was taken. A faint yellow extract composition was obtained by the preparation method similar to Example 1 except that spray drier of GA32 model was used to dewatering and drying. The productive rate was 0.21% of the original clam weight.

EXAMPLE 17

Clam meat from 3 kg of Cristaria plicata Lea was taken. A faint yellow extract composition was obtained by the preparation method similar to Example 1 except that ether was used to dewatering and drying. The productive rate was 0.25% of the original clam weight.

EXAMPLE 18

Clam meat from 3 kg of Cristaria plicata Lea was taken. A faint yellow extract composition was obtained by the preparation method similar to Example 1 except that a mixture of hydrochloric acid, citric acid and acetic acid in a rate of 1:1:1 was used instead of acetic acid. The productive rate was 0.63% of the original clam weight.

EXAMPLE 19

Clam meat from 3 kg of Cristaria plicata Lea was taken. A faint yellow extract composition was obtained by the preparation method similar to Example 1 except that the clam meat was smashed into particles of average size of 5 µm. The productive rate was 0.81% of the original clam weight.

EXAMPLE 20

Clam meat from 3 kg of Cristaria plicate Lea was taken. A faint yellow extract composition was obtained by the preparation method similar to Example 1 except that the clam meat was smashed into particles of average size of 20 µm. The productive rate was 0.23% of the original clam weight.

EXAMPLE 21

Clam meat from 3 kg of Cristaria plicata Lea was taken. A faint yellow extract composition was obtained by the preparation method similar to Example 1 except that the JL85-IB model of mincing machine was used for smashing. The productive rate was 0.11% of the original clam weight.

EXAMPLE 22

Clam meat from 3 kg of Cristaria plicata Lea was taken. A faint yellow extract composition was obtained by the preparation method similar to Example 1 except that no alkali and no ethanol in alkali treatment step were added, and the supernatant was ultrafiltered, concentrated by reverse osmose and directly freeze dried. The productive rate was 0.11% of the original clam weight.

EXAMPLE 23

Clam meat from 4 kg of Hyriopsis cumingii Lea was taken. The clam meat was smashed by a JM-85 model colloidal mill, and vaal water being 33% of the original clam weight was added. The mixture was then stirred and hydrochloric acid being 4% of the original clam weight was added. The mixture was heated at 88° C. for half an hour, then the suppernatant was taken and NaOH was added till pH value was 7.50. Then the mixture was left to stand and the precipitate was taken, and hydrochloric acid was added to the precipitate till the pH value was 5.5. Then the mixture was freeze dried to obtain a faint yellow extract composition. The productive rate was 0.15% of the original clam weight.

EXAMPLE 24

Clam meat from 7.5 kg of Cristaria plicata Lea was taken. The clam meat was smashed by a JM-85 model colloidal mill, and vaal water being 98% of the original clam weight was added. The mixture was then stirred and acetic acid being 12% of the original clam weight was added. The mixture was heated at 55° C. for 4.5 hours, then the suppernatant was taken and KOH was added till pH value was 13.50. Then the mixture was left to stand and the precipitate was taken, and acetic acid was added to the precipitate till the pH value was 7.0. Then the mixture was spray dried to obtain a faint brown extract composition. The productive rate was 0.65% of the original clam weight.

EXAMPLE 25

Clam meats from 4 kg of Hyriopsis cumingii Lea, 3 kg of Anodonta woodiana Lea and 3 kg of Cristaria plicata Lea were taken. The clam meat was smashed by a JM-85 Model colloidal mill, and vaal water being 65% of the original clam weight was added. The mixture then was stirred and the acid mixture of hydrochloric acid, acetic acid and citric acid, being 8.5% of the original clam weight was added. The mixture was heated at 66° C. for 2 hours, then the suppernatant was taken and NaOH was added till pH value was 10.5. Then the mixture was left to stand and the precipitate was taken and dehydration dried to obtain a faint yellow extract composition. The productive rate was 0.28% of the original clam weight.

EXAMPLE 26

Clam meat from 1.5 kg of Cristaria plicata Lea was taken. The preparation process was the same as that of Example 1. The obtained extract was extracted repeatedly for 4 times by the preparation process. A faint yellow extract composition was obtained and the productive rate was 0.06% of the original clam weight.

I claim:

1. A composition comprising a clam extract prepared from a clam from the group consisting of Anodonta woodiana Lea, Cristaria plicata, Hyriopsis cumingii or a mixture thereof, which is light yellow, yellow or light brown color, and has characteristic absorption in the range of 250 nm to 278 nm of ultraviolet-visible light absorption spectrum.

2. A process for preparing the clam extract composition of claim 1, comprising the steps of:

grinding clam meat;

treating the ground clam meat with acid and alcohol;

separating the acid-and-alcohol treated clam meat to obtain a clear liquid; and concentrating the clear liquid to give the clam extract composition.

3. The process according to claim 2, further comprising dehydration drying the concentrated substance or the precipitate.

4. The process according to claim 2, wherein pH value is 2.0–5.5 in the acid-and-alcohol treatment.

5. The process according to claim 2, wherein the acid is fatty acid with $C_2$–$C_8$ straight chain or branch chain, or hydrochloric acid.

6. The process according to claim 2, wherein the acid is acetic acid, citric acid, hydrochloric acid or a mixture thereof.

7. The process according to claim 2, wherein the average size of the ground clam meat is less than 1 mm.

8. The process according to claim 2, wherein the alcohol in the acid-and-alcohol treatment step is ethanol.

9. The process according to claim 2, wherein the alkali in the step of alkali treatment of the clear liquid is sodium hydroxide or potassium hydroxide.

10. The process according to claim 9, wherein pH value is 8–13 in the alkali treatment.

11. The process according to claim 9, wherein ethanol can be added in the step of alkali treatment.

12. The process according to claim 3, wherein the separated precipitate after the treatment of clear liquid with alkali is treated with acid before the freeze drying or spray drying.

13. A process for preparing the clam extract composition of claim 1, comprising the steps of:

grinding clam meat;

treating the ground clam meat with heat in the presence of acid and water;

separating the heat-treated ground clam meat to obtain a clear liquid;

concentrating the clear liquid to give the clam extract composition.

14. The process according to claim 13, further comprising dehydration drying of the concentrated substances.

15. The process according to claim 13, wherein the temperature of the heat treatment is 48°–88° C.

16. A clam extract composition prepared according to the process of claim 2.

17. A pharmaceutical composition for treatment of pain, comprising an effective amount of the clam extract composition of claim 1 and one or more pharmalogically acceptable carriers or excipients.

18. A method of treating pair in a patient in need thereof comprising administering an effective amount of the clam extract composition of claim 1.

19. The method of claim 18 wherein said administration comprises local administration of the extract to a part of the patient's body affected by said pain.

20. A process for preparing the clam extract composition of claim 1, comprising the steps of:

grinding clam meat;

treating the ground clam meat with acid and alcohol;

separating the acid-and-alcohol treated clam meat to obtain a clear liquid; and treating the clear liquid with alkali to give, by separation, a precipitate which is the clam extract composition.

* * * * *